(12) United States Patent
Ya'akov et al.

(10) Patent No.: US 7,474,911 B2
(45) Date of Patent: Jan. 6, 2009

(54) SYSTEM AND METHOD FOR MONITORING THE VOLUME OF URINE WITHIN A BLADDER

(75) Inventors: Ben Natan Ya'akov, Kfar Vradim (IL); Ofer Givati, Niagara-On-The-Lake (CA)

(73) Assignee: Solulearn Learning Solutions Ltd., Kfar Vradim (IL)

( * ) Notice: Subject to any disclaimer, the term of this patent is extended or adjusted under 35 U.S.C. 154(b) by 489 days.

(21) Appl. No.: 11/146,047

(22) Filed: Jun. 7, 2005

(65) Prior Publication Data

US 2006/0276707 A1    Dec. 7, 2006

(51) Int. Cl.
*A61B 5/05* (2006.01)
(52) U.S. Cl. ........................ 600/407; 702/156
(58) Field of Classification Search .......... 600/310, 600/407, 476, 473; 73/149; 702/156
See application file for complete search history.

(56) References Cited

U.S. PATENT DOCUMENTS

| | | | | |
|---|---|---|---|---|
| 4,729,245 A | * | 3/1988 | Hansman, Jr. | ............ 73/865 |
| 4,979,124 A | * | 12/1990 | Sachse et al. | ............ 702/38 |
| 5,103,835 A | | 4/1992 | Yamada et al. | |
| 5,235,985 A | * | 8/1993 | McMorrow et al. | ......... 600/443 |
| 5,964,710 A | | 10/1999 | Ganguly et al. | |
| 6,110,111 A | | 8/2000 | Barnard | |
| 6,319,208 B1 | | 11/2001 | Abita et al. | |

OTHER PUBLICATIONS

Hieda et al., Basic characteristics of the radio imaging method for biomedical applictions, Medical Engineering & Physics, vol. 26, 2004, pp. 431-437.*

* cited by examiner

*Primary Examiner*—Eric F Winakur
*Assistant Examiner*—Katherine L Fernandez
(74) *Attorney, Agent, or Firm*—Paul D. Bianco; Martin Fleit; Fleit Gibbons Gutman Bongini & Bianco PL (57) ABSTRACT

The proposed system introduces a multi-frequency electromagnetic wave analysis method for non invasive monitoring the volume of urine in the bladder. The innovation of the proposed system according to the present invention provides means for analyzing signal information received, after propagation via the bladder, by applying a pre-defined prediction function (resulting from the application of learning algorithm in conjunction with a Feature Extraction, algorithm for calculating the most contributing electromagnetic wavelengths, determining the most accurate measurements), and providing an accurate estimation of the volume of urine in the bladder.

21 Claims, 6 Drawing Sheets

SYSTEM AND METHOD FOR MONITORING THE VOLUME OF URINE WITHIN A BLADDER

BACKGROUND

The present invention relates to the use of electromagnetic waves for monitoring the volume of content within an enclosed media. More particularly, the invention relates to an electromagnetic wave analyzing method and system for monitoring the volume of urine in the bladder.

The urinary system is composed of two kidneys, two tubes called ureters, one urinary bladder, and the urethra. The kidneys are bean-shaped organs that produce urine. They are protected by fibrous connective as well as adipose tissue. The kidneys maintain homeostasis by regulating the water and salt balance as well as the pH of the blood, and they excrete nitrogenous wastes generated by amino acid, uric acid, and creatinine metabolism. The ureters are muscular tubes that lead away from a kidney and convey urine to the urinary bladder, which is a distensible, muscular organ that stores urine until it can be expelled. When the urinary bladder fills with urine to 250 of its total 600 milliliters and more, stretch receptors send impulses to the spinal cord. Urination results when returning nerve impulses cause the sphincters to relax and the bladder to contract, so, normal function of the lower urinary tract, including the bladder and the urethral control (sphincteric) mechanism depends on an intact spinal cord.

Urinary incontinence is the inability to control urination. The term may be used interchangeably with Over Active Bladder (OAB) which also includes the same frequency in urination and urinary urge. It is estimated that over 12 million Americans have urinary incontinence. Incontinence affects all ages, both sexes, and people of every social and economic level. It is also estimated that 15 to 30 percent of people over the age of 60 who live at home have incontinence. Women are twice as likely as men to have this condition. Bladder dysfunction can be caused by spinal cord injury, brain injury or diseases that impair the nerves to the motor neuron or upper motor neuron. Neurogenic bladder is a general diagnosis commonly used and refers to altered bladder function resulting from interrupted nerve innervation due to a lesion of the central or peripheral nervous system. Damage to nerve pathways at any point between the cortical center in the brain and the bladder can impair normal bladder function leading to incomplete bladder emptying. The type of bladder dysfunction seen depends on the exact site and the extent of the lesion. Diffuse neurologic damage, such as that from multiple sclerosis, Parkinson's disease or spinal cord injury can produce the inability to initiate or adequately complete voiding.

Post-void residual (PVR) urine volume is the volume remaining in the bladder immediately after completion of voiding (emptying). Knowing the PVR is important in patients suspected of incomplete bladder emptying or urinary retention. Usually, a person may maintain some ability to void, but elevated PVR lead to an increased risk of acute urinary retention, urinary tract infection, or upper tract pathology such as pyelonephritis, hydronephrosis or renal insufficiency. Urinary retention is determined by measuring the post-void residual (PVR) urine volume. A PVR volume of greater than 100 mL is generally accepted as the criteria to define urinary retention. In elderly patients, however, a PVR of 150 to 200 mL or greater indicates incomplete bladder emptying. Urine remaining in the bladder after the person has voided can become colonized with bacteria. The measurement of PVR urine volume is also an important component of continence assessment and bladder management during bladder retraining programs for patients with spinal cord and brain disorders which cause bladder dysfunction. Measurement of PVR urine volume provides quantitative feedback to the patient and the rehabilitation team about the effectiveness of the voiding technique.

The standard method of determining PVR urine volumes is intermittent catheterization, which is associated with increased risk of urinary infection, urethral trauma and discomfort for the patient. Bladder ultrasound scanning has been introduced as an alternative, noninvasive method, to avoid the potential complications of intermittent catheterization. Using this method, PVR urine volume can be measured immediately after a patient voids (if necessary, between scheduled catheterizations), which increases feedback about voiding technique used during bladder retraining. Early studies of ultrasound in this application were done using large scanners, which were relatively immobile. These ultrasound methods required separate calculation of the total bladder volume and of the PVR urine volume.

During the last decade there have been significant developments in bladder ultrasonography. Portable, battery-powered ultrasound devices have been developed specifically for the noninvasive measurement of total bladder volumes and/or PVR urine volumes. They consist of a hand-held ultrasound transducer (scanhead) and a base unit with a display screen. The scanhead is placed on the patients' abdomen (suprapubic area) and aimed toward the bladder. The unit calculates and displays the bladder volume.

Extreme obesity, severe abdominal scarring, pregnancy, muscle spasms, abdominal herniation and abdominal breathing may interfere with bladder ultrasound scanning and prevent accurate measurement.

The main question concerning the use of an ultrasound device to assess the PVR urine volume during bladder retraining is whether this method can accurately identify patients with more than 100 mL of urine in their bladders.

Several studies have been conducted to determine whether bladder ultrasound scanning for the measurement of PVR urine volume during bladder retraining in stroke patients and spinal cord injured patients is as accurate as the measurement obtained by catheterization. Results of these studies suggest that ultrasound measurements of PVR urine volume have some limitations in regard to accuracy. There is some opinion that more accurate results are obtainable through separate calculation than those that are automatically calculated by available ultrasound devices. Institutions using this technique should have appropriate training and operating protocols in place and be aware of its accuracy under local practice condition. The main problem in using such methods is the sensitivity to changes in the direction of the transducer. Ultrasonic systems are not automatic and require the intervention of a skilled user. Numerous attempts for monitoring the volume of urine in the bladder have been made in recent years. U.S. Pat. No. 6,319,208 discloses a urine monitor system, the system comprising a pressure measurement device capable of using magnetic induction telemetry. The invention may be used in measuring urinary tract pressure in diagnosing and treating urinary tract infections, anomalous bladder contraction, etc.

U.S. Pat. No. 5,964,710 proposes a system for estimating the volume of fluid in the bladder by sequentially scanning the bladder with ultrasonic beams that section the bladder into a number of transverse planes. After determining the area in each of the planes, the system determines the volume of the bladder by summing weighted version of the planar areas.

In addition, U.S. Pat. No. 6,110,111 includes means for automatically scanning the bladder of the user with ultrasound signals. The returning signals are used to calculate the volume of urine in the bladder and also to calculate the actual surface area of the bladder.

U.S. Pat. No. 5,103,835 proposes a monitoring device for preventing urinary incontinence which is based upon detection of electrical impedance. A monitoring device for preventing urinary incontinence has the following components: a high-frequency constant-current power supply adapted to supply a pair of terminals which are set on the surface of a human body across the urinary bladder; a high-frequency voltage signal detecting means which conducts wave detection from a high-frequency voltage signal sensed by a pair of sensing electrodes which are set on the human body surface at positions on the path of the high-frequency electrical current flowing between the pair of terminals;

In addition, U.S. Pat. No. 5,235,985 discloses an automatic bladder scanning apparatus. This apparatus is included in order to produce information concerning the three dimension image of the bladder, said information then used to calculate the bladder volume.

None of the existing methods and apparatuses described above proposes an apparatus which is non-invasive, automatically monitoring the bladder measurements, simple to use and cost effective.

The present invention evaluates bladder function without the use of invasive instrumentation, such as catheterization, using a multi-frequency electromagnetic wave analyzing method and apparatus for monitoring the volume of urine in the bladder.

SUMMARY OF THE PRESENT INVENTION

The present invention discloses an electromagnetic wave analysis system for monitoring volume of urine in a bladder. The system is comprised of a transmitter enabling transmission of multi-frequency signals, for transmitting electromagnetic wave signals towards the urine in the bladder; a receiver enabling to receive multi-frequency signals, for receiving the propagated electromagnetic wave signals; a Central Processing Unit (CPU), for analyzing the signals and quantifying the volume of urine in the bladder.

The signal analysis utilizes mathematical predication functions which represent the relation between the signal frequencies and bladder volume. The prediction function is defined by a kernel function. The prediction function of the analyzing process is based on a predefined sensitivity algorithm applied during the learning phase.

The learning phase is carried out during calibration stage enabling adjustment of the monitoring unit to a specific group of users, specific type of disorders or fine tuning to a specific user. Improved prediction accuracy can be achieved by the introduction of a predefined sensitivity algorithm, which utilizes a Feature Extraction Algorithm for improving range resolution of the signal.

The learning algorithm includes the following steps: performing measurements of the attenuate level of each signal at all frequencies at different levels of urine volume in the bladder; submitting all measurements to a learning algorithm for determining a predicting regression function; the determination of this predicting regression function is, therefore, based on invasive method measurements of volume of urine in a bladder.

The learning algorithm is optionally based on neural network technique or support vector machines or any other suitable machine learning technique. The information regarding the strengths of the signals propagated via the bladder is conveyed to a Central Processing Unit for computation, diagnosis and display/alarm. Also included in the present invention is an alarm unit for alerting of overfilling of the bladder and a display unit for presenting the measured volume of urine in the bladder.

The present invention includes electromagnetic wave analysis method for monitoring volume of urine in a bladder. The method is comprised of the following steps: transmitting electromagnetic wave signals of multi-frequencies towards the bladder; receiving the propagated electromagnetic wave signals via the bladder; analyzing electromagnetic wave signals by applying a predefined prediction function; and quantifying the volume of urine in the bladder. The method may also include the steps of displaying the volume of urine in the bladder, transmitting an alert of over-filling of the bladder and transmitting the information regarding the strengths of the signals propagated via the bladder to a remote station for computation, diagnosis and display/alarm.

BRIEF DESCRIPTION OF THE DRAWINGS

These and further features and advantages of the invention will become more clearly understood in the light of the ensuing description of a preferred embodiment thereof, given by way of example only, with reference to the accompanying drawings, wherein.

DETAILED DESCRIPTION OF THE PREFERRED EMBODIMENT

The proposed system introduces a multi-frequency electromagnetic wave analyzing method for monitoring the volume of urine in the bladder and the need to void. The electromagnetic waves are attenuated while passing through the bladder. Different attenuation is encountered at different frequencies. This phenomenon is used to determine, by applying Machine Learning algorithms, the amount of urine in the bladder. The innovation of the proposed system according to the present invention is the provision of means for analyzing information regarding the attenuated signals by applying a learning algorithm for calculating the volume of urine in the bladder. Further accuracy can be achieved by applying a sensitivity algorithm for the calculation of the most contributing electromagnetic wavelengths, determining the most useful combination of frequencies to be used in the analysis and hence an accurate estimation of the volume of urine in the bladder. These learning algorithms are mathematical methods which extract information concerning the pattern of these signals. Other existing methodologies usually fail to measure such information.

According to the present invention the encompassing effects of both electric and magnetic fields and their compounded effect at all levels (i.e. atomic, molecular, tissue) on wave propagation via the bladder and its immediate surroundings, are taken into consideration.

The learning algorithm has a central role in the first stage of the system's operation. It is used to calibrate the system to a specific group of patients (e.g. children, adult women or elderly men) or specific types of disorders. This calibration is achieved by measuring the attenuated levels of each electromagnetic signal at all frequencies, passing through the bladder. All measurements (attenuated signals and volume of urine in the bladder) are submitted to the learning algorithm in order to create a regression function for the determination of urine volume in the bladder. Urine volume levels in the bladder are measured using invasive measurements methods such as catheterization. The prediction phase uses the measured attenuations at the different frequencies and calculates the volume of the urine in the bladder. The sensitivity algorithm determines the most contributing frequencies to the prediction of the urine.

The established prediction function may then be fine-tuned for every patient by, once again, applying the learning algorithm procedure in order to adjust the regression function for a specific individual.

At the learning phase, the different attenuated level of each electromagnetic wavelength along with the pattern created from the attenuation of these electromagnetic waves at all frequencies is measured. At each frequency, a different attenuated signal is transmitted and registered. The pattern of the attenuations at all sampled frequencies corresponding to the current amount of urine in the bladder is then submitted to an initial learning algorithm such as a Support Vector Machine, neural network-or any other method known in the art. The mathematical function used to determine the volume of urine in the bladder is preferably defined by Kernel Functions. Kernels Methods provide pattern analysis algorithms which operate on various types of data and can detect different types of relations. Correlation, factor, cluster and discriminate analysis are just some of the types of pattern analysis tasks that can be performed on different data types such as sequences, text, images, graphs and vectors.

When using kernel methods for pattern recognition, the analyzed data is embedded into vector space and linear relations of the data are detected within the vector space. "Linear relations" can be regressions, classifications, correlations, principal components, etc. Many standard algorithms may be rewritten so that they only require inner products between data (inputs). Hence, when the proposed system is activated, the regression function calculates the volume of urine in the bladder using the attenuated signal levels of the electromagnetic wave as input.

Figure 1:
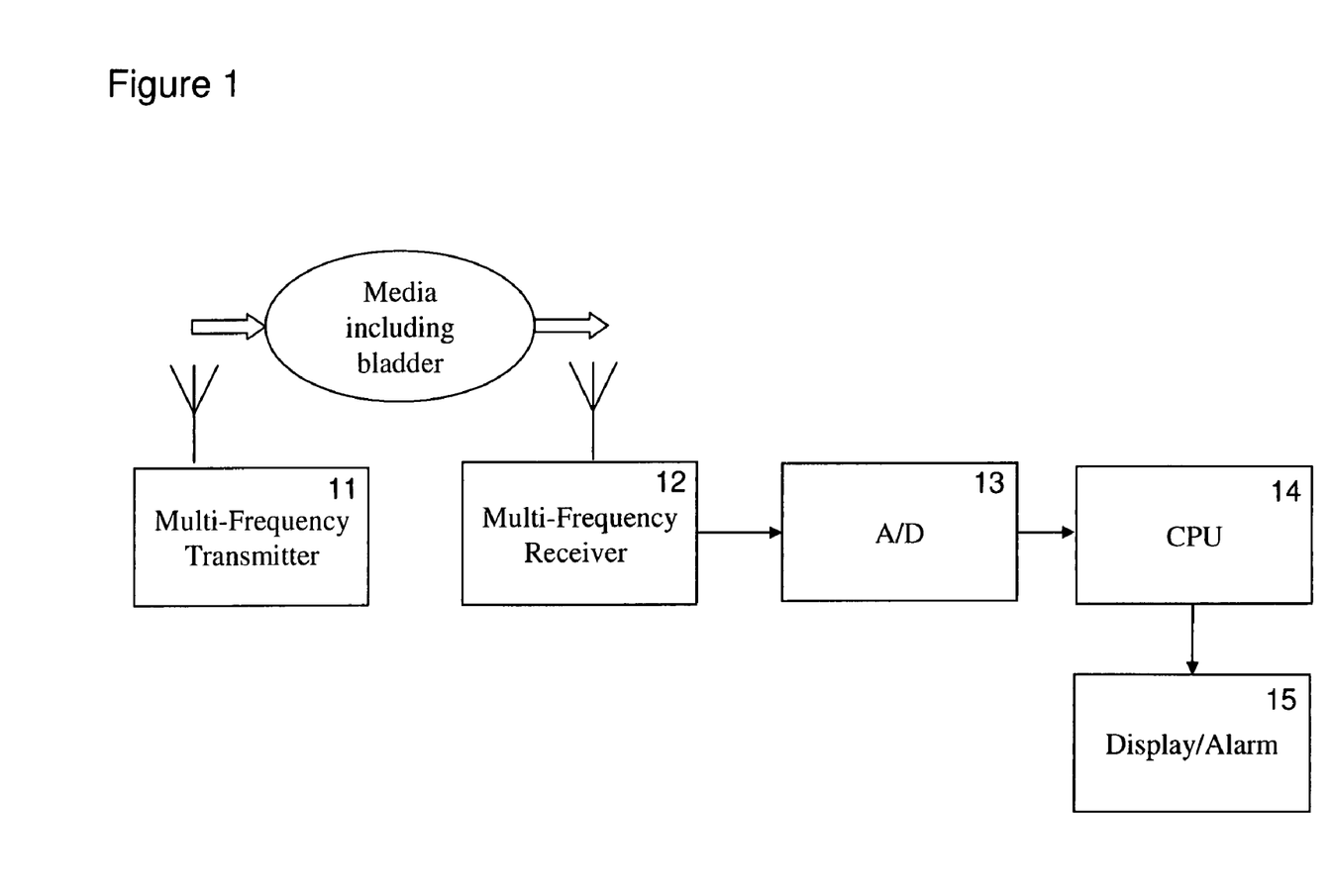
FIG. 1 is a block diagram of a basic wave-analyzing system according to a preferred embodiment of the present invention.

FIG. 1 is a block diagram of a basic wave-analyzing system according to the preferred embodiment of the present invention. The Multi-Frequency transmitter 11 transmits multi-frequency electromagnetic wave signals, at known power level over a wide frequency range via an antenna, towards the urine in the bladder. In order to obtain accurate estimate of urine volume in the bladder, the frequency ranges in which said electromagnetic waves are preferably defined is wide. The wavelengths should be of the order of a few centimeters and smaller, but not smaller than infrared wavelengths. For example, the frequency range 800-2500 MHz is considered sufficiently wide. The transmission of the signals is carried out via a suitable antenna operating in the vicinity of the body encasing the bladder. The Multi-Frequency receiver 12 is provided for receiving these electromagnetic signals via the appropriate antenna. The received signals regarding said electromagnetic waves are conveyed to the Analogue to Digital (A/D) conversion unit 13, which converts these signals into digital format. The signals' are submitted to the Central Processing Unit (CPU) 14 in digital form. The CPU 14 analyzes these signals strengths and computes the volume of urine in the bladder. The computation is supported by onboard software, whereas said software holds the necessary algorithms including the above mentioned learning algorithms or any other prediction algorithm. The computed volume of urine in the bladder is then conveyed to a Display/Alarm Unit 15, which either displays the results regarding the amount of urine in the bladder and/or functions as an alarm to prevent overfilling of the bladder.

Figure 2:
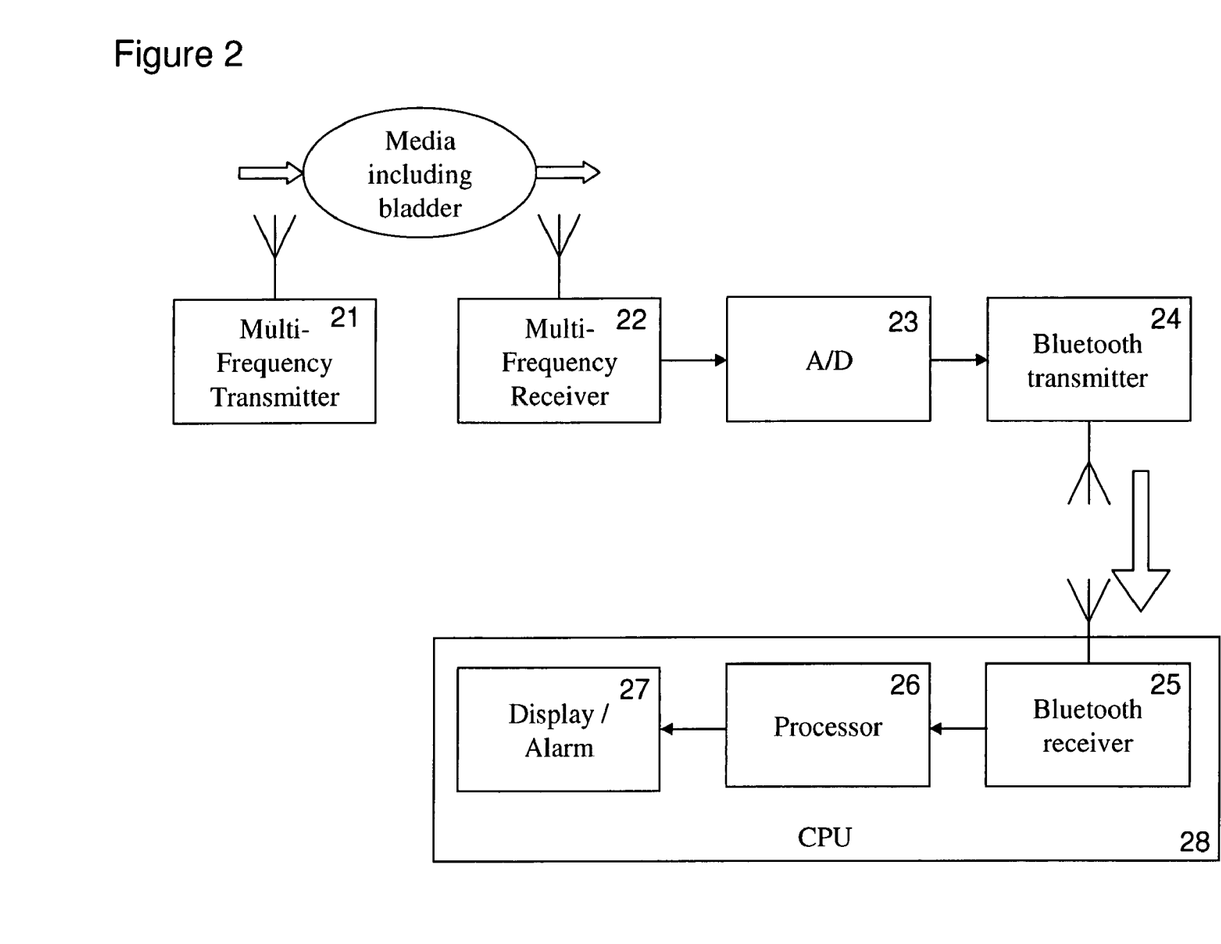
FIG. 2 is an illustration describing the components comprising an augmented wave-analyzing system to include supervisory station according to the present invention.

FIG. 2 is a block diagram illustrating the components comprising an augmented wave-analyzing system according to the present invention. The Multi-Frequency Transmitter 21 transmits multi-frequency electromagnetic waves over the predefined frequency range and power level, via an antenna, towards the urine in the bladder. The transmission of the signals is carried out via a suitable antenna operating in the vicinity of the body encasing the bladder.

Figure 3:
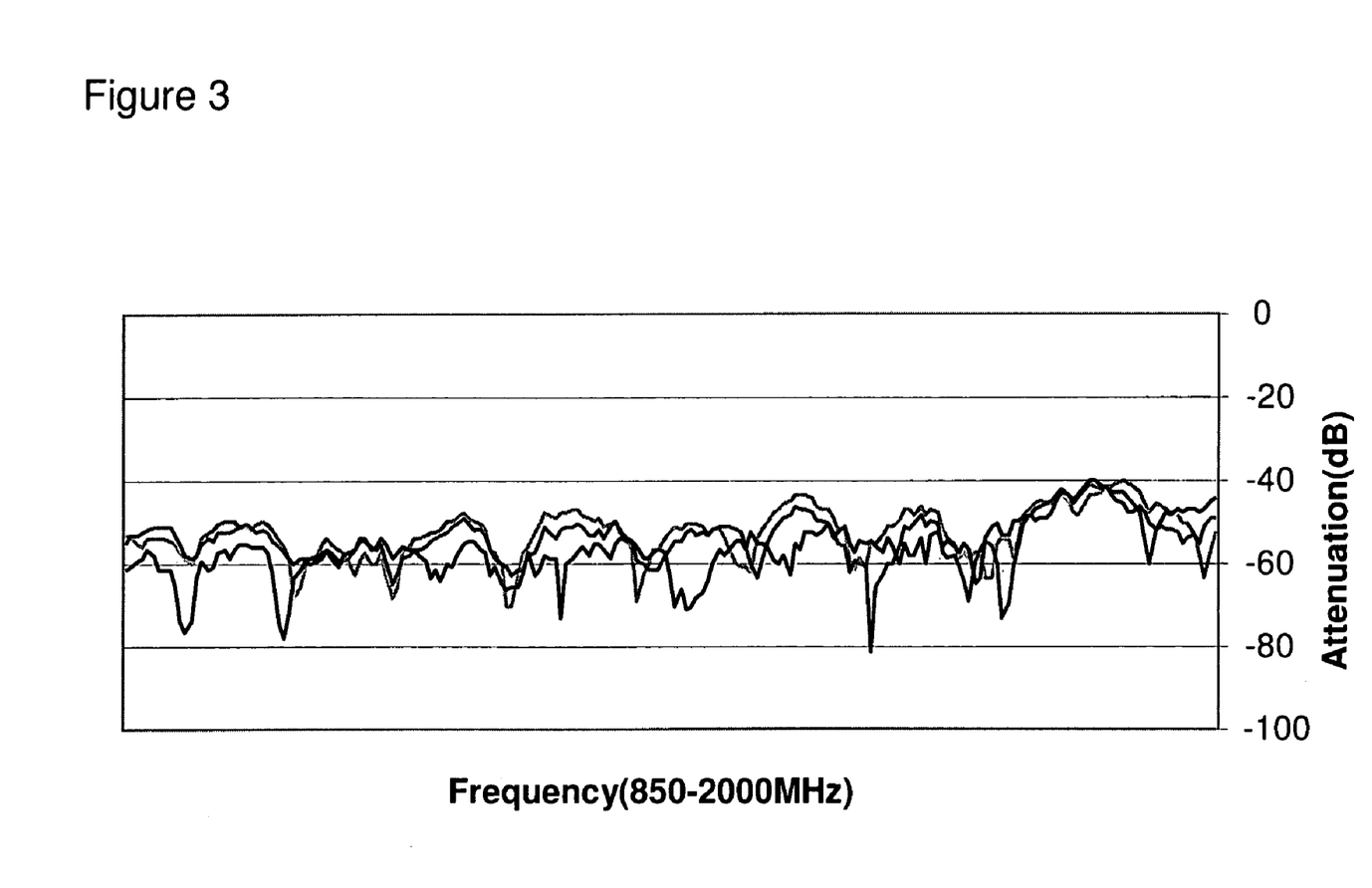
FIG. 3 illustrates patterns of wave attenuation of urine in the bladder received by three different bladder tests.

The Multi-Frequency Receiver 22 is provided for receiving these electromagnetic via an antenna. The received signals regarding said electromagnetic waves are conveyed to the Analogue to Digital (A/D) conversion unit 23, which converts these signals to digital format. The digital signals are then conveyed to the Signal Transmitter 24. The Signal Transmitter 24 transmits this information to a remote CPU 28, which functions as a nurse station, using Bluetooth or other types of wireless communication protocols. The Signal Receiver 25, located within the remote CPU 28, receives said signals, and transfers this information to the Processor 26, which computes the urine volume in the bladder. The measurements defining the volume of urine are then conveyed to the Display/Alarm unit 27, which displays the results regarding the amount of urine in the bladder and/or functions as an alarm and prevent overfilling of the bladder. Hence, the proposed configuration introduces an augmented wave-analyzing system provided to monitor the volume of urine in the bladder from a plurality of patients, such as a nursing station in an institution FIG. 3 illustrates patterns of wave attenuation due to propagation through media containing the urine in the bladder received by three different amount of urine in a particular bladder. The uppermost line depicts the pattern of wave attenuation when the bladder is full, whereas the bottom curve is obtained when the bladder is empty. Hence, the correlation of the volume of urine in the bladder with the pattern of appropriate electromagnetic waves is shown.

Figure 4:
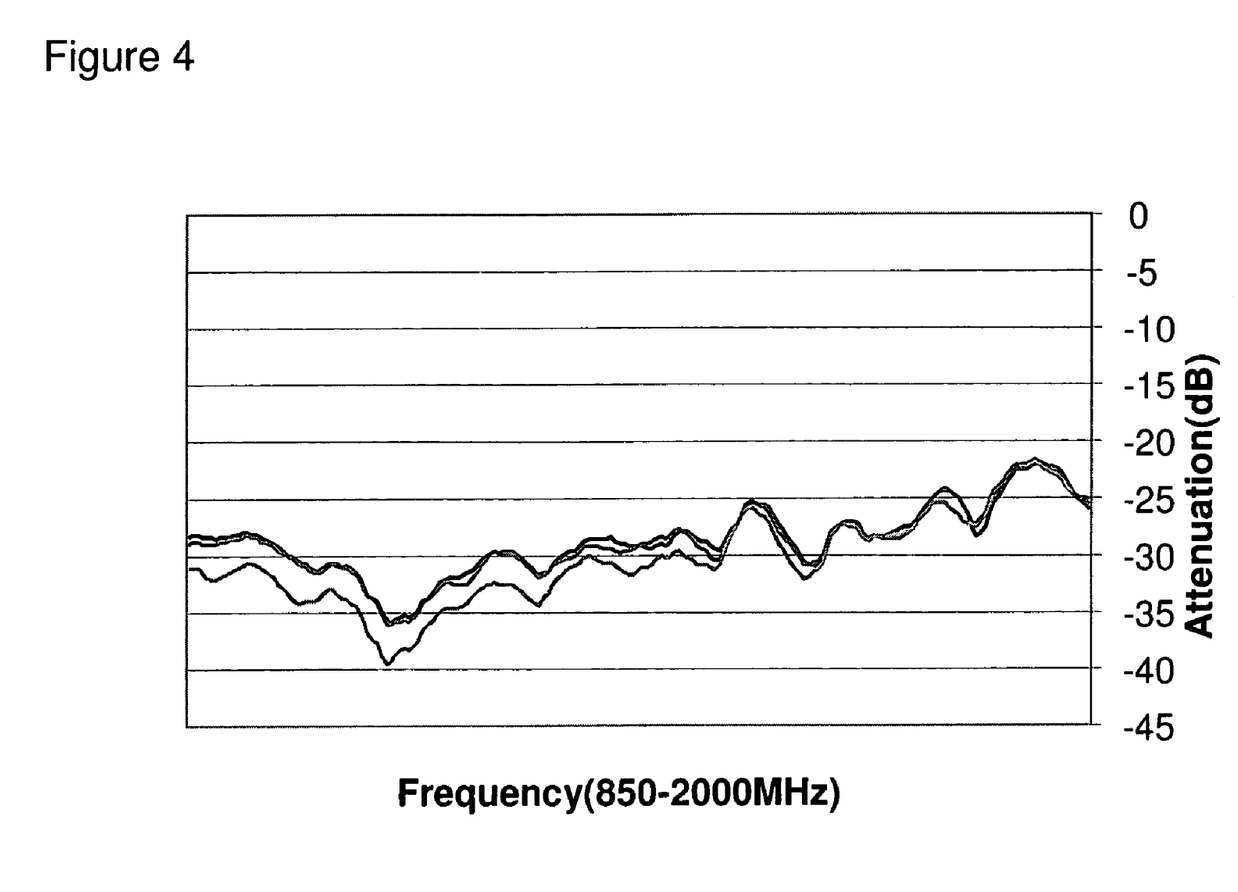
FIG. 4 illustrates three patterns of wave attenuation after propagation via different volumes of urine in a media.

FIG. 4 illustrates three patterns of wave attenuation due to propagation through urine in a media when contained in a glass jug. Upon comparison of FIG. 3 and FIG. 4 it is seen that the human body produces a different signal attenuation characteristic profile compare to that which is produced by a glass jug. Viewing the different patterns provides a good indication of the effect the bladder and its surrounding has on the propagated signals.

Figure 5:
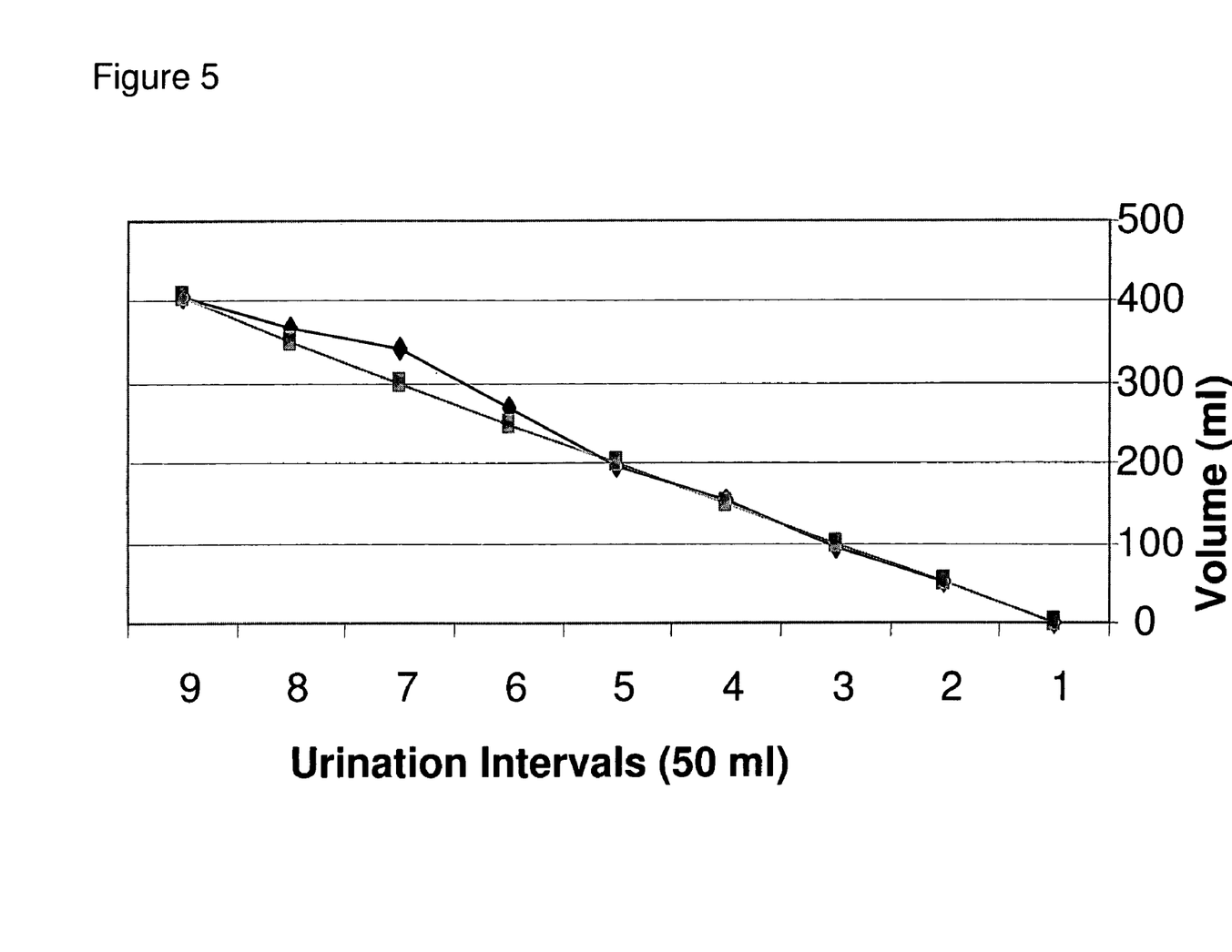
FIG. 5 illustrates the volume of urine, collected from the bladder into a jug, measured and predicted at urination intervals.

FIG. 5 illustrates the volume of urine collected from the bladder, during a single urination, into a jug in 50 ml intervals. The top line defines the predicted volume of urine in the media as computed by the proposed system, whereas the bottom line defines the actual measured volume of urine.

Figure 6:
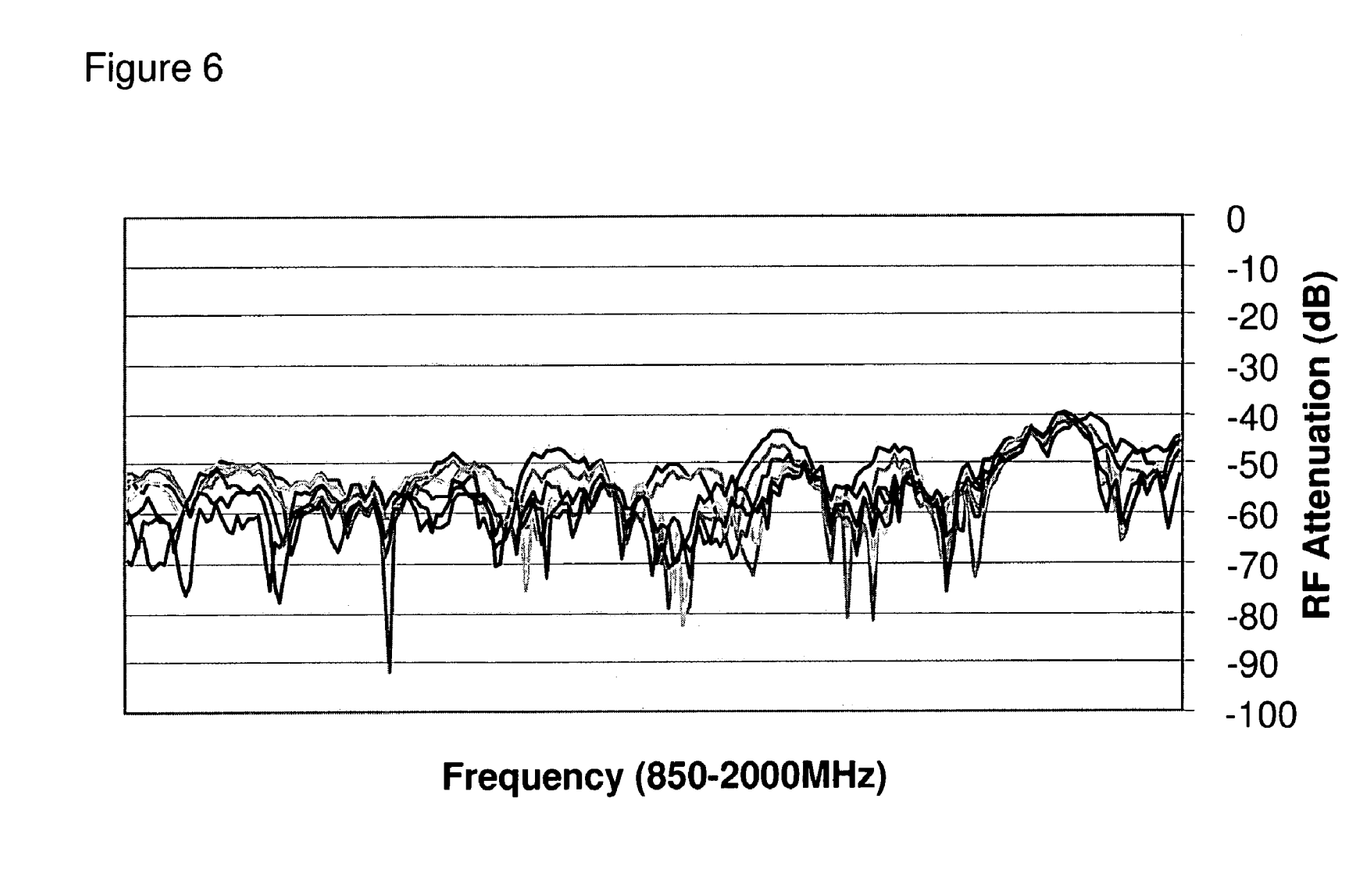
FIG. 6 illustrates seven different patterns of wave attenuation due to propagation through different volume of urine in the bladder.

FIG. 6 illustrates seven different patterns of wave attenuation due to propagation through urine in the bladder. The different patterns are obtained from measuring the electromagnetic wave signals at urination intervals of 50 ml. In order to predict the amount of urine in the bladder, the initial learning algorithm relates to each pattern as a different point in an n-dimensional Euclidian space, wherein n is the number of frequencies presented in the measurements. This algorithm provides a non-linear regression function within an n+1 Euclidean space, whereas the computed attenuation patterns are similar as possible to the measurements received during the learning phase. The different patterns are submitted to the regression function established by the learning algorithm, wherein each pattern represents different wave attenuation. As a result, the amount of urine in the bladder can be calculated.

The sensitivity analysis, according to the present invention, may be achieved by using any Feature Extraction algorithm thereby improving the estimation of urine volume in the bladder. In addition, the initial learning algorithm described above may further be carried out by other regression algorithms interpreting emitted waveforms other than electromagnetic radiation (such as reflected and/or propagated ultrasonic or sonic signals).

While the above description contains many specific examples by which this invention could be implemented, these should not be construed as limitations on the scope of the invention, but rather as exemplifications of the preferred embodiment. Those skilled in the art will envision other possible variations that are within its scope.

What is claimed is:

1. An electromagnetic wave analysis system for monitoring volume of urine in a bladder encased in a body, said urine bladder and body having unknown electromagnetic characteristics, said system comprised of:
    a transmitter enabling transmission of multi-frequency signals simultaneously, for transmitting multi-frequency electromagnetic wave signals simultaneously towards the urine in the bladder;
    a receiver enabling to receive multi-frequency signals simultaneously, for receiving the propagated electromagnetic wave signals;
    a Central Processing Unit (CPU), for analyzing the signals and quantifying the volume of urine in the bladder, wherein analyzing is achieved independently of prior knowledge of the electromagnetic characteristics of the urine, the bladder and the body encasing the bladder.

2. The system of claim 1 wherein the signal analysis utilizes mathematical predication functions which represent the relation between the signal frequencies and bladder volume and wherein said signal analysis comprises a calibration stage and wherein said predication functions comprise a learning phase utilizing a learning algorithm.

3. The system of claim 2 wherein the mathematical function is extracted from kernel function in accordance with a predefined sensitivity algorithm.

4. The system of claim 2, wherein the prediction function of the analyzing process is based on a predefined sensitivity algorithm applied during the learning phase.

5. The system of claim 3 wherein the learning phase is carried out during the calibration stage enabling adjustment of the monitoring unit to a specific group of users, specific type of disorders or fine tuning to a specific user.

6. The system of claim 3, wherein the predefined sensitivity algorithm utilizes a Feature Extraction Algorithm for improving range resolution of the signal.

7. The system of claim 3, wherein the predefined sensitivity algorithm is achieved by applying an initial learning algorithm.

8. The system of claim 3, wherein the learning algorithm includes the following steps:
    performing measurements of the attenuate level of each signal at all frequencies at different levels of urine volume in the bladder;
    submitting all measurements to a learning algorithm for determining a predicting regression function, said regression based on invasive method measurements of volume of urine in a bladder.

9. The system of claim 3, wherein the learning algorithm is based on a neural network technique.

10. The system of claim 1, wherein the information regarding the strengths of the signals propagated via the bladder is transmitted to a remote station for computation, diagnosis and display/alarm.

11. The system of claim 1, further comprising an alarm unit for alerting of overfilling of the bladder.

12. The system of claim 1 further comprising a display unit for presenting the volume of urine in the bladder as measured.

13. An electromagnetic wave analysis method for monitoring volume of urine in a bladder encased in a body, the method comprising the steps of:
    simultaneously transmitting electromagnetic wave signals of multi-frequencies towards the bladder;
    simultaneously receiving the propagated multi-frequencies electromagnetic wave signals via the bladder;
    analyzing electromagnetic wave signals by applying a predefined prediction function wherein analyzing is achieved independently of prior knowledge of the electromagnetic characteristics of the urine, the bladder and the body encasing the bladder; and
    quantifying the volume of urine in the bladder based on the electromagnetic wave signal analysis.

14. The method of claim 13 wherein the signal analysis utilizes kernel functions, which represent the relation between the signal frequencies and bladder volume.

15. The method of claim 13, further comprising the step of displaying the volume of urine in the bladder.

16. The method of claim 13, further comprising the step of transmitting an alert of over-filling of the bladder.

17. The method of claim 13, wherein the pre-defined sensitivity algorithm utilizes a Feature Extraction Algorithm for identifying the most contributing wavelengths.

18. The method of claim 13, wherein the predefined sensitivity algorithm is achieved by applying an initial learning algorithm.

19. The method of claim 13, wherein the learning algorithm is carried out by a Support Vector Machine.

20. The method of claim 13 further comprising the step of transmitting the information regarding the strengths of the signals propagated via the bladder to a remote station for computation, diagnosis and display/alarm.

21. The method of claim 13 further comprising the step of transmitting an alert of overfilling of the bladder.

* * * * *